United States Patent [19]
Ehrreich et al.

[11] 3,983,249

[45] Sept. 28, 1976

[54] METHOD FOR TREATING ANGINA PECTORIS WITH CERTAIN N-ARYLSULFONYL-N'(AZA-3-BICYCLOALKYL) UREAS

[75] Inventors: Stewart J. Ehrreich, Suffern, N.Y.; Lester Zitowitz, West Orange, N.J.

[73] Assignee: Science Union et Cie Societe Francaise de Recherche Medical, France

[22] Filed: Dec. 26, 1974

[21] Appl. No.: 536,669

Related U.S. Application Data

[63] Continuation of Ser. No. 381,958, July 23, 1973, abandoned, which is a continuation-in-part of Ser. No. 347,245, March 30, 1973, abandoned.

[52] U.S. Cl. ............................................. 424/321
[51] Int. Cl.² ...................................... A61K 31/18
[58] Field of Search ............................. 424/321

[56] References Cited
UNITED STATES PATENTS 3,136,814   6/1964   Irikura et al. ............... 260/326.23

FOREIGN PATENTS OR APPLICATIONS 1,153,982   6/1969   United Kingdom ........... 260/326.23

*Primary Examiner*—James O. Thomas, Jr.
*Assistant Examiner*—Daren M. Stephens
*Attorney, Agent, or Firm*—Gordon W. Hueschen

[57] ABSTRACT

This application is directed to certain novel sulfonyl urea compounds, to their use as antianginal agents, and to the use of certain prior art sulfonyl ureas as antianginal agents. The sulfonyl ureas are characterized in that they are N-arylsulfonyl-N'-methyl-N'(aza-3-bicycloalkyl) ureas and N-arylsulfonyl-N'-(aza-3-bicycloalkyl) ureas.

5 Claims, No Drawings

METHOD FOR TREATING ANGINA PECTORIS WITH CERTAIN N-ARYLSULFONYL-N'(AZA-3-BICYCLOALKYL) UREAS

This application is a continuation application, of our copending application Ser. No. 381,958, filed July 23, 1973 now abandoned, which in turn is a continuation-in-part of application of our copending application, Ser. No. 347,245, filed Mar. 30, 1973, now abandoned.

This invention relates to certain novel compositions of matter classified as N-phenylsulfonyl-N'-methyl-N'-aza-bicycloalkyl ureas, to processes for their preparation and using such compositions as antianginal agents, and to the method of using certain related N-phenylsulfonyl-N'-aza-bicycloalkyl ureas as antianginal agents.

The novel N-phenylsulfonyl-N'-methyl-N'-(aza-3'-bicycloalkyl) ureas have the structural formula:

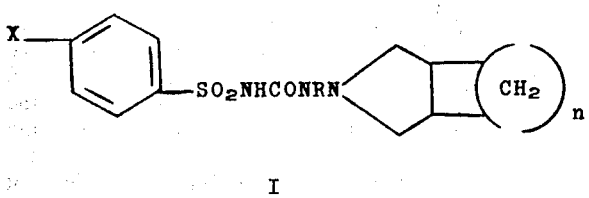

I and the pharmaceutically acceptable salts thereof, wherein X represents chloro, bromo, methyl and hydrogen, R represents methyl and n is an integer from 1–3.

In general, the compounds of this invention (I) may be prepared by reacting an X-substituted phenylsulfonyl carbamic ester, or a functional derivative thereof, with equivalent or slightly excess quantities of an N-methylamino-aza-3-bicycloalkane according to techniques analogously described in the prior art (J. Org. Chem. 23, 927, 1958). It is advantageous to effect the foregoing condensation by heating the reactants together within the temperature range of about 90°–150°C, preferably at about reflux temperatures, said reaction preferably being conducted in the presence of an inert solvent such as toluene, benzene and the like. This reaction may be depicted as follows:

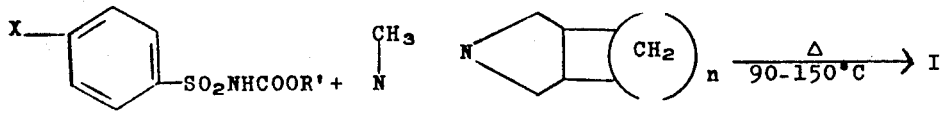

II                            III wherein X and n are as previously defined and R' is any desired lower hydrocarbon residue, preferably ethyl. Alternatively, the desired final compounds of Formula I can be prepared by condensing the appropriate sulfonyl icocyanate with the N-alkyl-aza-3-bicycloalkane in an inert solvent, preferably benzene.

The starting X-substituted phenyl sulfonyl urethanes of Formula II may readily be prepared by reacting an X-substituted phenylsulfonamide with a hydrocarbon residue chlorocarbonate, e.g. ethyl chlorocarbonate in the presence of an alkali metal carbonate according to prior art techniques.

The starting methylamino-aza-3-bicycloalkanes (III) can be prepared by nitrosating the appropriate aza-bicycloalkanes with nitrous acid (produced in situ as described below) and reducing the resulting N-nitroso-aza-3-bicycloalkane with lithium aluminum hydride according to standard techniques well known in the art. Other reducing agents may similarly be used to reduce the N-nitroso compound. Since the reduction of the N-nitroso compound is highly exothermic, it is well to bring the reactants together slowly, such as by gradual addition of the N-nitroso compound in an inert solvent (e.g. anhydrous ether) to the reaction mixture containing the lithium aluminum hydride reducing agent. The N-methylation of the amino-aza-3-bicycloalkane to the desired N-substituted compound of Formula III is effected according to standard techniques. One such technique is the admixture of the N-aminoaza-3-bicycloalkane with a dimethyl sulfate in the presence of a strong base, e.g. sodium hydroxide, keeping the stirred mixture at a temperature of about 10°–15°C. The aza-3-bicycloalkanes are known compounds and are more specifically described in Belgian Pat. No. 693702 and others such as provided by the Derwent Abstracting Service under basic abstract 28266.

The following examples are illustrative of the methods of preparation of the compounds of Formula I.

Preparation of Starting Materials

EXAMPLE I

N-Amino-aza-3-bicyclooctane

A. N-Nitroso-aza-3-bicyclooctane

Dissolve 44 g. of aza-3-bicyclooctane in 32 ml. of concentrated hydrochloric acid and 16 ml. of water. With continuous stirring heat the solution to 75°–80°C and in a dropwise fashion add a solution of 34 g. of sodium nitrite in 50 ml. of water (during and after the addition, add small amounts of 2N hydrochloric acid to keep the solution strongly acidic). After the addition is complete, continue heating (70°–75°C) with stirring for 2 hours. Cool and filter the precipitate and recrystallize the air-dried product from hexane to yield N-nitroso-aza-3-bicyclooctane.

B. N-Amino-aza-3-bicyclooctane

At the reflux temperature of the reaction mixture add, in a dropwise fashion, with stirring, a solution of 28 g. of N-nitroso-aza-3-bicyclooctane in 200 ml. of anhydrous ether to 11.4 g. of lithium aluminum hydride in 300 ml. of ether. Stir the mixture at reflux for 20–24 hours and decompose the reaction by the cautious addition of water. Filter and concentrate the ethereal filtrate on a steam bath to obtain crude N-amino-aza-3-bicyclooctane, which is used without further purification.

EXAMPLE II

N-Methylamino-aza-3-bicyclooctane

Dissolve 25.2 g. of N-amino-aza-3-bicyclooctane in 10 g. of sodium hydroxide and 100 ml. of water. With cooling (10°–15°C) and constant stirring, add, in a dropwise fashion, 25.2 g. of dimethyl sulfate. Stir the mixture for 4 hours keeping the reaction mixture strongly alkaline with 15% sodium hydroxide. Extract the product with ether. Dry the ethereal filtrate and distill to obtain N-methylamino-aza-3-bicyclooctane.

Preparation of Final Compounds

EXAMPLE III

N-(p-chlorophenylsulfonyl)-N'(methyl)-N'[aza-3-bicyclo (3,3,0)octyl]urea

To a solution of 46.2 g. of ethyl p-chlorophenylsulfonyl carbamate in 150 ml. of dry toluene, add, in a dropwise fashion, a solution containing 28.0 g. of N-methylamino-aza-3-bicyclooctane in 100 ml. of toluene. With stirring, heat the reaction mixture at reflux temperature for 3 hours and allow the product to crystallize by cooling to room temperature. Filter and suspend the crude product in 250 ml. of water and acidify with 5% hydrochloric acid. After 5–10 minutes of vigorous stirring, filter and air dry the filtered product which is recrystallized from a mixture of chloroform-petroleum ether to yield N-(p-chlorophenylsulfonyl)-N'-(methyl)-N'[aza-3-bicyclo-(3,3,0) octyl]urea.

Thus, by following the standard procedures for the preparation of this type compound there are produced N-(4-methylbenzenesulfonyl)-N'-methyl-N'-[aza-3-bicyclo (3,3,0)octyl-3] urea; N-(benzenesulfonyl)-N'-methyl-N'-[aza-3-bicyclo (3,3,0) octyl-3] urea; N-(4-chloro-benzenesulfonyl)-N'-methyl-N'-[aza-3-bicyclo(3,1,0) hexyl-3]urea; N-(4-bromo-benzenesulfonyl)-N'-methyl-N'-[aza-3-bicyclo (3,3,0) octyl-3] urea; N-(4-methylbenzenesulfonyl)-N'-methyl-N'[aza-3-bicyclo (3,2,0) heptyl-3] urea; N-(benzene-sulfonyl)-N'-methyl-N'[aza-3-bicyclo (3,2,0) heptyl-3] urea; N-(4-chloro-benzenesulfonyl)-N'-methyl-N'-[aza-3-bicyclo (3,2,0) heptyl-3] urea; N-(4-methyl-benzenesulfonyl)-N'-methyl-N'-[aza-3-bicyclo (3,2,O) hexyl-3] urea.

The antianginal agents of this invention are those compounds having the structural formula:

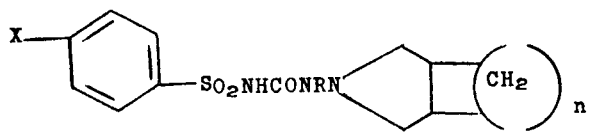

IV and the pharmaceutically acceptable salts thereof wherein X represents chloro, bromo, methyl and hydrogen, R represents hydrogen and methyl, and $n$ is an integer 1 to 3.

The method for the prevention of the symptoms of angina pectoris (i.e. severe sub-sternal pain, dyspnea, and hypoxic changes in limb-lead electrocardiogram, e.g. depression of the S-T segment, as well as other well-known factors associated with angina pectoris) is effected by administering a therapeutically effective quantity of an N-arylsulfonyl-N-(aza-3-bicycloalkyl) urea (IV) of this invention. The therapeutically effective dose for the treatment of angina pectoris is determined by modified Rona and Stanton procedures for producing cardiac necrosis, in rats, as follows:

Male Charles River rats, not less than 200 gms. are used exclusively. The animals are conditioned at least one week before any drug is given. Animals of comparable age and body weights are separated into control and experimental groups and allowed standard lab chow and water ad libitum. The provoking drug is 80 mg./kg. of di-isoproterenol HCl (ISU) injected subcutaneously once per day for two days. The control group receives an isovolumic injection of physiological saline by the same route. The experimental group receives an appropriate dose of test compound intraperitoneally or orally two days prior to the start of ISU injection. ISU is started on the third day of the drug regimen, and both agents are given to their respective groups for the following two days. The experimental drug is given as two equally divided doses each day; on days three and four it is given 30 minutes before and 30 minutes after ISU. A fourth group of rats received ISU, s.c., plus 250 ug. kg. of nitroglycerine as a drop of solution on the oral mucous membranes 5, 30, 60 and 90 minutes after the ISU challenge. The nitroglycerin group determines the sensitivity of any given litter of rats to this standard antianginal agent. The initial and final body weights of all animals are recorded, and then they are sacrificed 24 hours after the second ISU injection. The heart of each animal is removed, blotted dry, weighed, and graded for degree of necrosis. Four areas of the heart are examined for lesions, the apex, interventricular septum, left ventricle, and right ventricle. A 0–4 grading system is used as follows:

0 = no lesions.
1 = mottling of apex and distal left ventricle.
2 = well demarcated necrotic areas on apex.
3 = large infarct-like necrosis in the left ventricle extending to the intraventricular septum.
4 = large infarct-like necrosis involving both ventricles and the intraventricular septum.

Scoring may also be made at 0.5, 1.5, 2.5, and 3.5 degrees of severity. An average necrosis score for each group is determined and a percent protection is calculated.

Following the collection of these data an evaluation is completed by the use of modern day statistical analysis techniques. Using these techniques a program has been designed which computes the percentage of heart weight to body weight, and the mean, variance, standard deviation and standard error of these percentages. One-way analysis of variance is performed on inter-group scores of necrosis for statistical evaluation.

From this assay, as well as by comparison with other prior art compounds useful in the treatment of angina pectoris, the compounds of this invention exert their antianginal effect within the dosage range of about 10 to 50 mg./kg. of body weight with 20 mg. being the preferred oral dosage.

Of course, the ultimate dosage of the compounds of this invention will depend upon the severity, the stage and the individual characteristics of each case and will be finally determined by the attending diagnostician by the use of standard and recognized parameters for this purpose. Preferred compounds for this invention are those wherein X represents methyl and R represents either hydrogen or methyl and N is 3.

In addition to the antianginal activity of the compounds of formula I it is also found that such compounds are hypoglycemic. The dose range for such compounds can readily be determined by standard assay techniques such as is described as follows: Charles River male CD strain rats and male CF 1 mice (20–25 grams) are fed ad libitum until the start of each experiment. The hypoglycemic agent is solubilized by homogenizing in 0.1N NaOH and is administered orally. A volume of 0.5 ml. is given to a 25 gram mouse and 2 ml. is given to a 250 gram rat. The pH of these solutions ranges between 8 to 10. In some experiments, Diazoxide is administered intraperitoneally to induce hypoglycemia. The pH for Diazoxide solutions is about 10.5. Alkaline water adjusted to the appropriate pH was administered in place of compounds to control animals. Periodically, the test rat is temporarily anesthetized and bled from the dorsal aorta and the plasma was used to determine glucose levels in the rat. Periodically, the test mice are temporarily anesthetized and are bled from the orbital sinus and whole blood was used to determine glucose levels using the Technicon Auto-Analyzer (modification of the ferricyanide method of Hoffman).

From the foregoing test procedure and by other standard laboratory techniques, as well as by comparison with well-known hypoglycemic agents, i.e. those compounds of Formula IV (other than those embraced by Formula I), the therapeutically effective dosage range for lowering blood sugar levels of compounds of Formula I is determined.

Perhaps as part of the mechanism by which the compounds of this invention function in their use as antianginal agents is that they are especially effective in increasing the nutritional blood flow in the heart (i.e. that it opens or enlarges small capillaries of the heart facilitating better blood flow to the heart muscle). This quality of opening small capillaries is especially useful in the treatment of those patients wherein coronary vascular constriction has occurred. Support for this characteristic can be demonstrated by the technique wherein there is utilized an ischemic or hypoxic challenge in a discrete localized area of the ventricular myocardium as described by the following methodology:

Mongrel dogs (15–25 kg.) of either sex are anesthetized with 35 mg./kg. of sodium pentobarbital. A cuffed endotracheal tube is inserted and the dog maintained on positive pressure artificial respiration using room air through a Harvard respirator. A femoral vein is cannulated and connected to a saline infusion for drug injection and anesthesia supplement, and a femoral artery is cannulated for systemic blood pressure measurement using a Statham P23 AA transducer. The left chest is opened at the fourth intercostal space, and the pericardium exposed and opened to form a pericardial cradle presenting the entire left heart. At this point the braches given off by the left anterior descending coronary artery are examined, and one that serves a relatively small area of epi- and andocardium is selected by gross observation for cannulation. Each dog has a different pattern of branching off the left anterior descendens, and so there cannot be uniformity in the branch selected for cannulation from dog to dog. After selection of one appropriate coronary artery branch, the left common carotid artery is cannulated and blood flow from the carotid artery is led through an extracorporeal square wave electromagnetic flow meter to an Intramedic Luer-end catheter which enters the small coronary branch. When the system is complete, a small coronary artery subserving a discrete area of the left ventricular myocardium is autoperfused from a common carotid artery at the existing systemic blood pressure. The flow into the coronary branch can be measured as well as the perfusion pressure, but also, and more important, the flow can be totally controlled by clamping or partially occluding appropriate cannulae. A second flow prob is put around the ascending aorta to monitor cardiac output.

Two 38 gauge platinum electrodes are inserted (3–4 mm) into the subepicardium served by the cannulated artery to record electrograms from this area. Each electrode is insulated along its entire length except at the tip, and connected so that a monopolar recording, equivalent to a "V-lead" setting can be made. A miniature Brody-Walton strain gauge is sewn to the ventricular surface close to the electrodes to provide a measure of the contractile force/beat, velocity of contraction, and the differential $dF/dt$ for later calculations of work. The design when complete makes possible the following measurements and calculations:

1. Systemic blood pressure.
2. Any limb lead ECG.
3. Myocardial electrograms.
4. Cardiac output and peripheral resistance.
5. Coronary artery branch flow, pressure and resistance in that vascular bed.
6. Contractile force/beat and velocity of contraction and relaxation:
7. Time-tension index.
8. Heart rate.

Each subject acted as its own control, and the preparation was useful only for the evaluation of drugs with relatively short onset times and duration.

Each experiment started with an electrogram equilibration period since initial recordings were for the most part due to an injury current produced when the electrodes were inserted. Since the electrograms recorded were not comparable to any standard ECG recordings which are familiar clinically, simultaneous myocardial electrograms and limb lead II recordings were observed and comparisons were made to verify which standard wave forms could be identified. These evaluations determined the ventricular components to be used in the succeeding tests.

After electrogram stabilization occurred and injury currents disappeared, the heart was ready for control challenge. Each experiment started with a one minute occlusion of the arterial inflow to the cannulated LAD branch. Records were taken at standard ECG paper speed of 25 mm/sec. at 15 second intervals. At the end of the one minute occlusion, flow into the coronary branch artery was allowed to resume and records were monitored at 30 seconds after occlusion and at subsequent one minute intervals until the control configuration was reobtained. Control challenges were repeated at 30 minute intervals using this procedure over a period for six hours. Ten dogs were used for these control studies, and the data was analyzed to ascertain the change of response with time and to establish differences from control values within confidence limits of 90, 95 and 99 percent. After control changes were established it was found that 1.0 mg./kg. of drug protects the subject against these ischemia-induced changes.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms, as for example, tablets, capsules and suppositories, or in liquid forms as for example, elixirs, emulsions and injectables. In the formulation of pharmaceutical preparations there can be employed such substances which do not react with the active substances as for example, water, gelatin, lactose, starches, magnesium stearate, calcium carbonate, talc, vegetable oils, benzyl alcohols, gums, polyalkylene glycols, petroleum jelly and the like. The active ingredient of such pharmaceutical preparations is preferably present in the preparation in such proportions by weight that the proportion by weight in the active ingredient to be administered lies between 0.1 and 50 percent.

Tablet Formulation

The following formulation provides for the manufacture of 1,000 tablets:

|     |                                                          | Grams |
| --- | -------------------------------------------------------- | ----- |
| (1) | 1-(3-azabicyclo[3,3,0]oct-3-yl)-<br>3-(p-tolylsulfonyl) urea | 25    |
| (2) | Lactose, U.S.P.                                          | 181   |
| (3) | Corn Starch, U.S.P.                                      | 92.5  |
| (4) | Magnesium Stearate                                       | 1.5   |

Thoroughly granulate a mixture of 92.5 g. of corn starch and the lactose with a paste prepared by dissolving 20 gm. of corn starch in 100 ml. of hot distilled water. Dry the resulting granulation at 40°–45°C and pass it through a No. 16 mesh screen. To the dried, screened granulation add a blended mixture of the active ingredient (1) and the magnesium stearate. Thoroughly blend and then press into tablets of 300 mg. each.

Capsule Formulation

The following formulation provides for the manufacture of 1,000 capsules:

|     |                                                                  | Grams |
| --- | ---------------------------------------------------------------- | ----- |
| (1) | 1-methyl-1-(3-azabicyclo[3,3,0]oct-3-yl)-<br>3-(p-tolylsulfonyl) urea | 25    |
| (2) | Lactose                                                          | 273.5 |
| (3) | Magnesium Stearate                                               | 1.5   |

Mix active ingredient (1) with the lactose and blend in the magnesium stearate. Fill hard gelatin capsules with 300 mg. each of the blended mixture to produce capsules containing 25 mg. of 1-methyl-1-(3-azabicyclo[3,3,0]oct-3-yl)-3-(p-tolylsulfonyl) urea.

Parenteral Formulation

The following formulation provides for the manufacture of 1,000 vials each containing 10 mg. of active ingredient:

|     |                                                    |       |      |
| --- | -------------------------------------------------- | ----- | ---- |
| (1) | 1-(3-azabicyclo[3,3,0]oct-3-yl)-3-<br>(p-tolylsulfonyl) urea | gm    | 10.0 |
| (2) | Monobasic potassium phosphate                      | gm    | 6.0  |
| (3) | Water for injection, U.S.P. q.s.                   | liter | 1.0  |

Dissolve ingredients (1), (2) and (3) in approximately 80 percent of the volume of water and filter the resulting solution. Add to the filtrate sufficient water to make to a 1000 ml. volume. Sterile-filter the solution and aseptically fill one milliliter vials, then lyophilize. After the lyophilized cake is dry, aseptically stopper the vials with rubber plugs and seal.

We claim:

1. A method for the prevention and reversal of the symptoms of angina pectoris which comprises administering to a host suffering from angina pectoris a therapeutically effective quantity of a compound of the formula

or a pharmaceutically acceptable salt thereof, wherein X is hydrogen, chloro, bromo and methyl, R is methyl or hydrogen and *n* is an integer from 1 – 3.

2. A method according to claim 1 wherein X is methyl, R is hydrogen and N is 3.

3. A method according to claim 1 wherein X is chloro, R is hydrogen and N is 3.

4. A method according to claim 1 wherein X is chloro, R is methyl and N is 3.

5. A method according to claim 1 wherein X is methyl, R is methyl and N is 3.

* * * * *